US012672787B2

(12) United States Patent
Yliluoma et al.

(10) Patent No.: US 12,672,787 B2
(45) Date of Patent: Jul. 7, 2026

(54) NOSE PAD ASSEMBLY FOR MEASURING HEART RATE, AND OPTICAL APPARATUS AND METHOD EMPLOYING SAID ASSEMBLY

(71) Applicant: Pixieray Oy, Espoo (FI)

(72) Inventors: Timo Yliluoma, Helsinki (FI); Juha Virtanen, Helsinki (FI); Klaus Melakari, Espoo (FI); Ari Pitkänen, Vantaa (FI)

(73) Assignee: Pixieray Oy, Espoo (FI)

( * ) Notice: Subject to any disclaimer, the term of this patent is extended or adjusted under 35 U.S.C. 154(b) by 0 days.

(21) Appl. No.: 19/068,137

(22) Filed: Mar. 3, 2025

(65) Prior Publication Data

US 2025/0281055 A1 Sep. 11, 2025

(30) Foreign Application Priority Data

Mar. 5, 2024 (FI) ..................................... 20245272

(51) Int. Cl.
*A61B 5/024* (2006.01)
*A61B 5/00* (2006.01)
(52) U.S. Cl.
CPC ...... *A61B 5/02427* (2013.01); *A61B 5/02438* (2013.01); *A61B 5/6803* (2013.01);
(Continued)
(58) Field of Classification Search
CPC ........... A61B 5/02438; A61B 5/02427; A61B 5/6803; A61B 5/742; A61B 5/7475;
(Continued)

(56) References Cited

U.S. PATENT DOCUMENTS

| | | | |
|---|---|---|---|
| 7,648,463 | B1 | 1/2010 | Elhag et al. |
| 2004/0059212 | A1 | 3/2004 | Abreu |

(Continued)

FOREIGN PATENT DOCUMENTS

| | | |
|---|---|---|
| WO | 2015054681 A1 | 4/2015 |
| WO | 2017001955 A1 | 1/2017 |

OTHER PUBLICATIONS

N. Constant, O. Douglas-Prawl, S. Johnson and K. Mankodiya, "Pulse-Glasses: An unobtrusive, wearable HR monitor with Internet-of-Things functionality," 2015 IEEE 12th International Conference on Wearable and Implantable Body Sensor Networks (BSN), Cambridge, MA, USA, 2015, pp. 1-5 (Year: 2015).*

(Continued)

*Primary Examiner* — Chao Sheng
(74) *Attorney, Agent, or Firm* — ZIEGLER IP LAW GROUP, LLC.

(57) ABSTRACT

Disclosed is a nose pad assembly for measuring heart rate, said assembly including: a first cushioning element (FCE) and a second cushioning element (SCE), wherein a first inner surface of FCE and a second inner surface of SCE are capable of redirecting light, a light transmitting element arranged in FCE; a light sensing element arranged in SCE; and processor(s) arranged in a bridge portion of an optical apparatus in which said assembly is employed. The processor(s) is/are configured to: control light transmitting element to emit light, wherein the light passes through the user's nose towards light sensing element, and wherein at least a portion of the light is redirected by: the first inner surface, the second inner surface; and process sensor data to determine heart rate.

19 Claims, 3 Drawing Sheets

(52) U.S. Cl.
CPC ............ *A61B 5/742* (2013.01); *A61B 5/7475* (2013.01); *A61B 2560/0462* (2013.01); *A61B 2562/0238* (2013.01); *A61B 2562/185* (2013.01); *A61B 2562/227* (2013.01)

(58) Field of Classification Search
CPC .... A61B 2560/0462; A61B 2562/0238; A61B 2562/185; A61B 2562/227
See application file for complete search history.

(56) References Cited

U.S. PATENT DOCUMENTS

| | | |
|---|---|---|
| 2010/0210926 A1 | 8/2010 | Ciancitto et al. |
| 2011/0166462 A1 | 7/2011 | Iijima et al. |
| 2016/0120421 A1 | 5/2016 | Matsuo et al. |
| 2017/0164848 A1* | 6/2017 | Nadeau .............. A61B 5/14552 |
| 2019/0239770 A1 | 8/2019 | Komoda et al. |
| 2023/0172468 A1* | 6/2023 | Kaplan .................. A61B 5/332 600/470 |
| 2023/0210389 A1* | 7/2023 | Yang .................... A61B 5/1455 600/310 |

OTHER PUBLICATIONS

Finnish Patent and Registration Office, Search Report, Application No. 20245272, Mailed Jun. 7, 2024, 2 pages.

\* cited by examiner

NOSE PAD ASSEMBLY FOR MEASURING HEART RATE, AND OPTICAL APPARATUS AND METHOD EMPLOYING SAID ASSEMBLY

TECHNICAL FIELD

The present disclosure relates to nose pad assemblies for measuring heart rates. The present disclosure also relates to optical apparatuses incorporating such nose pad assemblies. The present disclosure further relates to methods for measuring heart rates using such nose pad assemblies.

BACKGROUND

In recent years, there has been a growing interest in the field of wearable health monitoring devices, driven by an increasing demand for non-invasive and continuous health monitoring solutions. For example, some existing wearable devices (for example, such as wristbands, smartwatches, eyeglasses, and the like) are equipped with optical sensors to measure a heart rate of a user. Such wearable heart rate monitoring devices provide accessibility, convenience, and portability to the user for measuring the heart rate.

However, existing wearable heart rate monitoring devices have certain limitations associated therewith. Firstly, such existing wearable devices are not reliable enough for measuring the heart rate with a high accuracy. This is because their optical sensor performance is adversely affected, for example, by user movement, user's skin tone variations, and other environmental factors (such as ambient light, humidity, temperature, and the like). This affects an overall performance of such existing wearable devices, and results in inaccurate heart rate measurements. For example, some optical sensors arranged on a temple or a nose bridge of a pair of the eyeglasses often rely on reflective optical measurements for measuring the heart rate. These optical sensors are extremely sensitive to a relative movement of the pair of the eyeglasses with respect to user's skin. Moreover, a distance between a given optical sensor and the user's skin may also vary from zero to several millimetres, depending on a shape of user's head. In addition to this, when the eyeglasses are worn by the user, hair may also fall in between the user's skin and the given optical sensor. These aforesaid factors adversely affect signal-to-noise ratio of such reflective optical measurements, and the heart rate is inaccurately measured. Furthermore, the reflective optical measurements are often unreliable, as they are sensitive to user's skin perfusion which could vary with an ambient temperature and/or a body temperature. Secondly, a prolonged use of such existing wearable devices often leads to discomfort due to their tight fit on user's skin. Moreover, some existing wearable devices employ tethered clip-on optical sensors for measuring the heart rate. However, such tethered clip-on sensors are bulky and uncomfortable to users, which reduces user experience when such existing wearable devices are to be used during physical activities.

Therefore, in light of the foregoing discussion, there exists a need to overcome the aforementioned drawbacks.

SUMMARY

The present disclosure seeks to provide a nose pad assembly, an optical apparatus, and a method for measuring heart rate in a highly accurate and reliable manner, by way of redirecting light that passes through user's nose when measuring the heart rate. The aim of the present disclosure is achieved by a nose pad assembly, an optical apparatus incorporating such a nose pad assembly, and a method for measuring heart rate using such a nose pad assembly, as defined in the appended independent claims to which reference is made to. Advantageous features are set out in the appended dependent claims.

Throughout the description and claims of this specification, the words "comprise", "include", "have", and "contain" and variations of these words, for example "comprising" and "comprises", mean "including but not limited to", and do not exclude other components, items, integers or steps not explicitly disclosed also to be present. Moreover, the singular encompasses the plural unless the context otherwise requires. In particular, where the indefinite article is used, the specification is to be understood as contemplating plurality as well as singularity, unless the context requires otherwise.

DETAILED DESCRIPTION OF EMBODIMENTS

Figure 1:
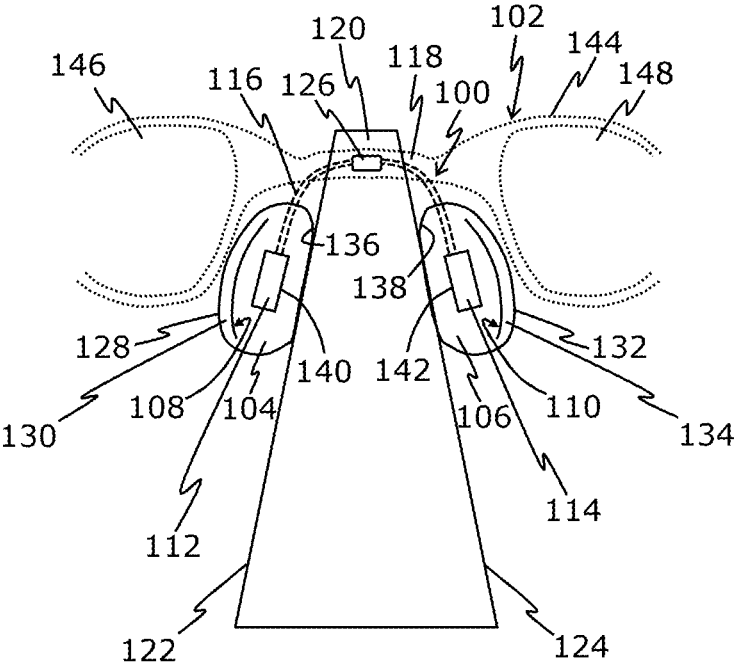
FIG. 1 illustrates a nose pad assembly for measuring heart rate, in accordance with an embodiment of the present disclosure.

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In a first aspect, an embodiment of the present disclosure provides a nose pad assembly for measuring heart rate, the nose pad assembly comprising:

a first cushioning element and a second cushioning element, wherein a first inner surface of the first cushioning element and a second inner surface of the second cushioning element are capable of redirecting light;

a light transmitting element arranged in the first cushioning element;

a light sensing element arranged in the second cushioning element; and at least one processor arranged in a bridge portion of an optical apparatus in which the nose pad assembly is employed, wherein when the optical apparatus is worn by a user, the bridge portion is in proximity of the user's nose such that the first cushioning element rests on a first side of the user's nose and the second cushioning element rests on a second side of the user's nose, wherein the at least one processor is configured to:

control the light transmitting element to emit light, wherein the light passes through the user's nose towards the light sensing element, and wherein at least a portion of the light is redirected by at least one of: the first inner surface, the second inner surface, during said passage; and process sensor data, collected by the light sensing element, to determine the heart rate of the user.

In a second aspect, an embodiment of the present disclosure provides an optical apparatus comprising:

a frame employed to hold an optical element per eye, wherein a bridge portion of the frame rests on a user's nose when the optical apparatus is worn by the user; and a nose pad assembly of the first aspect, wherein the nose pad assembly is attached to the bridge portion of the frame.

In a third aspect, an embodiment of the present disclosure provides a method for measuring heart rate using a nose pad assembly of the first aspect, the method comprising:

controlling a light transmitting element, arranged in a first cushioning element, for emitting light, wherein the light passes through a user's nose towards a light sensing element arranged in a second cushioning element, and wherein at least a portion of the light is redirected by at least one of: a first inner surface of the first cushioning element, a second inner surface of the second cushioning element, during said passage; and processing sensor data, collected by the light sensing element, for determining the heart rate of the user of an optical apparatus in which the nose pad assembly is employed.

The present disclosure provides the aforementioned nose pad assembly, the aforementioned optical apparatus, and the aforementioned method for measuring the heart rate in a highly accurate and reliable manner, by way of redirecting the light that passes through the user's nose when measuring the heart rate. The nose pad assembly utilises the first inner surface and the second inner surface for redirecting the light to maximize a transmission of the light from the light transmitting element towards the light sensing element, in order to determine the heart rate highly accurately and reliably, as compared to the prior art techniques. Beneficially, determining the heart rate in this manner is not affected, for example, due to any user movement, user's skin tone variations, environmental factors (such as ambient light, humidity, temperature, and the like), a relative movement of a pair of the eyeglasses with respect to user's skin, a shape of user's head, hair of the user, user's skin perfusion, and the like. The first cushioning element and the second cushioning element are designed to provide consistent skin contact with high comfort and light weight, and thus the optical apparatus can be used for extended periods for continuous and unobtrusive heart rate monitoring. Furthermore, the nose pad assembly is susceptible to employed in any type of optical apparatus (such as a pair of glasses, a pair of sunglasses, smart glasses, and the like). The nose pad assembly, the optical apparatus, and the method are simple, robust, fast, reliable, supports real time heart rate determination, and can be implemented with ease.

Throughout the present disclosure, the term "nose pad assembly" refers to a set of components that are collectively capable of measuring the heart rate, when the nose pad assembly is employed in the optical apparatus worn by a user. Throughout the present disclosure, the term "optical apparatus" refers to an apparatus that is to be worn over eyes of the user. Examples of such an optical apparatus include, but are not limited to, a pair of glasses, a pair of sunglasses, and smart glasses.

Throughout the present disclosure, the term "cushioning element" refers to an element that rests on a given side of the user's nose, and is capable of accommodating any one of: the light transmitting element, the light sensing element therein. A given cushioning element is designed to provide a soft and a supportive surface to the user's nose, when the nose pad assembly is in use (namely, when the optical apparatus is worn by the user). It will be appreciated that the first side could be one of a left side and a right side of the user's nose, whereas the second side could be another of the left side and the right side of the user's nose. The term "given cushioning element" encompasses the first cushioning element and/or the second cushioning element.

Notably, when the first inner surface of the first cushioning element and the second inner surface of the second cushioning element are capable of redirecting light, this mean that when the light incident on the first inner surface and the second inner surface, an optical path of the light would be redirected (namely, changed or altered) as required. The technical benefit of redirecting the light is that it facilitates in maximizing a transmission of the light from the light transmitting element towards the light sensing element, in order to determine the heart rate highly accurately and reliably, as compared to the prior art techniques. Herein, the term "redirecting" encompasses both reflection and backscattering of the light upon striking the first inner surface and the second inner surface. The term "given inner surface" refers to a surface of a given cushioning element that is capable of redirecting the light, when the light incidents on said surface. The term "given inner surface" encompasses the first inner surface and/or the second inner surface.

Optionally, the nose pad assembly further comprises an arm element that physically connects the first cushioning element and the second cushioning element through the bridge portion of the optical apparatus. Herein, the term "arm element" refers to a mechanical element that is capable of physically connecting the first cushioning element and the second cushioning element through the bridge portion of the optical apparatus. It will be appreciated that the arm element may not necessarily be implemented as one single arm element, but could be implemented as two (separate) arm elements, wherein one of the two arm element connects the first cushioning element through the bridge, and another of the two arm elements connects the second cushioning element through the bridge.

Throughout the present disclosure the term "bridge portion" refers to a portion of the optical apparatus that rests on the user's nose when the optical apparatus is worn by the user. The bridge portion can be a central portion of the frame of the optical apparatus that holds the optical element per eye. It will be appreciated that the frame of the optical apparatus is designed in a manner that the optical element is firmly arranged on the frame. In an example, when the optical apparatus is implemented as a pair of eyeglasses, the frame may hold two optical elements, wherein a first optical element is employed for a first eye of the user, and a second optical element is employed for the second eye of the user. It will be appreciated that a material of the frame could be plastic, metal, polymer, and the like. Optionally, the optical element is implemented as one of: a planoconvex lens, a concavo-convex lens, a double convex lens, a biconvex lens, a planoconcave lens, a double concave lens, a biconcave, a bifocal lens.

Optionally, in the nose pad assembly:

the arm element and a given cushioning element are implemented as separate individual elements, wherein the arm element is arranged on one of: the bridge portion of the optical apparatus, a rim of a frame of the optical apparatus, or the arm element and a given cushioning element are integrated as a single element, wherein the given cushioning element is at least one of: the first cushioning element, the second cushioning element.

In this regard, in one implementation, the arm element that is arranged on one of: the bridge portion, the rim, physically connects the first cushioning element and the second cushioning element to the optical apparatus. Herein, the term "rim" refers to a part of the frame of the optical apparatus that holds and surrounds a given cushioning element. It will be appreciated that such an implementation may allow users to personalise nose pad assemblies (for example, by choosing different types/styles of arms and cushioning elements) based on their comfort and required aesthetics. In other implementations, the arm element and the given cushioning element are made as the single element (for example, such a single mechanical element), wherein said single element physically connects the first cushioning element and the second cushioning element to the optical apparatus. It will be appreciated that such an implementation may enhance modularity and ensures a seamless and ergonomic design of the nose pad assembly, thereby providing a streamlined and cohesive appearance to the nose pad assembly, whilst maintaining a comfort of the user using the nose pad assembly. It will be appreciated that when the optical apparatus is implemented as a pair of standard plastic eyeglasses in which there are no adjustable nose pads, and if height adjustment is needed in this scenario it may be done using adhesive filler pieces. In such a case, reflective photoplethysmography may be an integral part of a frame of the optical apparatus, and the first cushioning element and the second cushioning element of the nose pad assembly form an integral part of said frame.

Optionally, the arm element comprises electrical circuitry to electrically connect the light transmitting element with the at least one processor, and to electrically connect the light sensing element with the at least one processor. In this regard, since the light transmitting element and the light sensing element are to be controlled by the at least one processor, the electrical circuitry is required for electrically connecting the light transmitting element and the light sensing element with the at least one processor. It will be appreciated that the arm element serves as a mechanical component (as discussed earlier) as well as an electrical component in the nose pad assembly. It will also be appreciated that the electrical circuitry may comprise a flex printed circuit board (PCB) assembly and/or structurally integrated conductors (such as lead wires). The flex PCB assembly may be designed to conform to a shape of the arm element.

Throughout the present disclosure, the term "light transmitting element" refers to an element that is capable of emitting light. Examples of the light transmitting element include, but are not limited to, a light-emitting diode (LED), and a laser. The laser may be a vertical-cavity surface-emitting laser (VCSEL), an edge-emitting laser (EEL), or the like. Throughout the present disclosure, the term "light sensing element" refers to an element that is capable of sensing light. Examples of the light sensing element include, but are not limited to, a photodiode, a phototransistor, a photonic sensor.

Notably, the at least one processor controls an overall operation of the nose pad assembly. The at least one processor is communicably coupled to the light transmitting element and the light sensing element. The at least one processor could be implemented as any one of: a microprocessor, a microcontroller, or a controller. As an example, the at least one processor could be implemented as an application-specific integrated circuit (AISC) chip or a reduced instruction set computer (RISC) chip. It will be appreciated that at least one processor may not necessarily be arranged in the nose portion of the optical apparatus.

Typically, when the light passes through the user's nose, the light interacts with blood vessels present in the user's nose. As a heart of the user beats, it pumps blood through the blood vessels which cause variations in blood volume in the blood vessels (due to a pulsatile nature of blood flow). This results in changes in absorption of the light by the light sensing element. Notably, when the light emitted from the light transmitting element passes through the user's nose, at least the portion of the light is redirected by the at least one of: the first inner surface, the second inner surface, in order to maximize a transmission of the light from the light transmitting element toward the light sensing element. Upon passage, the light is detected at the light sensing element and a corresponding analogue electrical signal (namely, an electrical signal indicative of an amount of the (received) light) is generated as the sensor data. In other words, the light sensing element detects a variation of an intensity of the light caused by the pulsatile blood flow in the user's nose, to determine the heart rate of the user. Optionally, when processing the sensor data, the at least one processor is configured to: identify at least two consecutive highest points in the variation of the intensity of the light (in form of analogue electrical signals), wherein each highest point corresponds to a heartbeat of the user; and calculate a time between the at least two consecutive highest points to determine the heart rate of the user. The heart rate of the user may, for example, be expressed in terms of beats per second (BPS), beats per minute (BPM), or similar. Techniques for determining the heart rate using the light are well-known in the art.

Optionally, a material of the first cushioning element and the second cushioning element is soft and flexible and is only transparent for the light that is used for measuring the heart rate. In this regard, the first cushioning element and the second cushioning element are made up of soft materials, for example, such as silicones, polymers, or similar. The technical benefit of using the soft materials is that they provide a comfort (due to a cushioning effect) to the user's nose when the nose pad assembly is in use. This may, particularly, be beneficial in a scenario when the optical apparatus (in which the nose pad assembly is employed) is to be worn by the user for a considerably long time. Moreover, the soft materials may also facilitate in preventing the optical apparatus from sliding down the user's nose. The technical benefit of the material being flexible is that it allows the first cushioning element and the second cushioning element to adapt to a contour (namely, shape) of the user's nose, and facilitates having an optimum contact with skin of the user's nose when the nose pad assembly is in use. This would also ensure a proper alignment of the light transmitting element and the light sensing element, for accurately measuring the heart rate. Furthermore, the material of the first cushioning element and the second cushioning element is selectively transparent, i.e., said material would only allow specific wavelength(s) of the light used for measuring the heart rate to pass through the user's nose. This potentially minimises an interference from ambient light, and thus contributes to accurate heart rate determination.

Optionally, the light is one of: near-infrared light, green light, red light, white light. Typically, different wavelengths of light interact with biological tissues in the human body in different ways. For example, the near-infrared light penetrates relatively deeper into the biological tissues, while the green light and the red light are readily absorbed by haemoglobin present beneath skin's surface. The technical benefit of employing the near-infrared light is that it facilitates in an invisible operation of the nose pad assembly for measuring the heart rate (as the near-infrared light is not visible to the human eye). The near-infrared light also enables for a maximum sunlight rejection, thus high-quality and reliable sensor data is collected by the light sensing element, to determine the heart rate. Instead of employing the near-infrared light, one of: the green light, the red light, the white light can also be employed. The green light may be employed to enable additional measurements for blood flow characteristics when measuring the heart rate, whereas the red light may be employed for an improved signal strength, for collecting the sensor data. Optionally, a wavelength range of the near-infrared light is 700 nanometers (nm) to 1400 nm. As an example, the light used for measuring the heart rate may have a wavelength of 940 nm. Optionally, a wavelength range of the red light is 620 nm to 700 nm. Optionally, a wavelength range of the green light is 500 nm to 570 nm. In an example, the near-infrared light may be preferred over the red light due to a stronger absorption of oxyhaemoglobin by the near-infrared light at the wavelength of 940 nm, as compared to a wavelength of 660 nm of the red light. It will be appreciated that the green light may be beneficially employed when the heart rate is to be measured using reflective photoplethysmography (PPG), because light absorption of blood is high for the green light, and thus a signal-to-noise ratio may be high, even though the green light does not penetrate much deeper in the user's skin, as compared to other types of light. The near-infrared light may penetrate deeper in nose tissue as compared to the green light, but a backscattered signal of the near-infrared light is low. In addition to this, light absorption of blood is low for the near-infrared light, the signal-to-noise ratio tends to be very small for the near-infrared light. With the near-infrared light, a transmissive geometry would be advantageous, because the near-infrared light penetrates much deeper in the nose tissue, and thus can travel from one side of the nose to another side of the nose easily. Because of a long optical path, a modulation from pulsating blood is strong, and such a transmissive measurement picks up signals from deeper tissues of the nose, thus the measurement of the heart rate may be less sensitive to skin perfusion changes.

Optionally, the first cushioning element and the second cushioning element are removably attached to the light transmitting element and the light sensing element, respectively. In this regard, the first cushioning element and the second cushioning element could be removed (namely, detached) from and/or attached to the light transmitting element and the light sensing element, respectively, as and when required. Beneficially, this facilitates maintenance and cleaning of the first cushioning element and the second cushioning element. This may, particularly, be beneficial for a user who has allergies or a sensitive skin. Furthermore, this may also facilitate the user to replace the first cushioning element and/or the second cushioning element, for example, in case of any damage or wear. It will be appreciated that the first cushioning element and the second cushioning element could be in snug fit with the light transmitting element and the light sensing element, respectively, to be removably attached with them. The first cushioning element and the second cushioning element are removably attached to the light transmitting element and the light sensing element, respectively, by way of employing one of: a clip mechanism, a slide-in mechanism, a screw mechanism, a magnetic mechanism.

Optionally, the at least one of: the first inner surface, the second inner surface, is made of at least one of: a reflective material, a non-reflective material that is coated with a reflective material. In this regard, for the first inner surface and the second inner surface to be capable of redirecting the light, the first inner surface and/or the second inner surface is/are made of at least one of: the reflective material, the non-reflective material that is coated with the reflective material. It will be appreciated that a reflective material of the first inner surface facilitates in reflecting (namely, bouncing back) the light emitted by the light transmitting element towards the light sensing element through the user's nose. This increases a portion of the light (upon transmitting through the user's nose) available for detection by the light sensing element, thereby resulting in highly accurate determination of the heart rate. Moreover, a reflective material of the second inner surface may also facilitate in reflecting the light received from the light transmitting element (upon transmitting through the user's nose) towards the light sensing element. It will also be appreciated that the reflective material may, for example, be a pure reflective material such as aluminum, silver, or similar. However, in some cases, a pure reflective material may reflect the light in all directions, potentially wasting a considerable portion of the light. Therefore, the non-reflective material with a coating of the reflective material may be used for making the at least one of: the first inner surface, the second inner surface. The reflective material could be used as a reflective paint or a reflective film. Examples of the non-reflective material may include, but are not limited to, a polymer, a fabric, and a ceramic. The non-reflective material may act as a filter or diffuser, for reducing unwanted noise or light reflections within the nose pad assembly.

Optionally, the first inner surface and the second inner surface are concave in shape, a radius of said concave shape being selected so as to maximize the transmission of the light from the light transmitting element to the light sensing element. In this regard, the concave shape of the first inner surface and the second inner surface is determined as being concave with respect to an optical path of the light. In other words, while being transmitted from the light transmitting element to the light sensing element, the light is incident upon and redirected by an inwardly-curved (i.e., concave) surface of the first inner surface and the second inner surface. Notably, a concave shape (namely, a paraboloid shape) of the first inner surface and the second inner surface facilitates in redirecting and focusing a maximum portion of the light from the light transmitting element to the light sensing element in a manner that maximizes an interaction of said light with tissues and blood vessels inside the user's nose. This results in an improved power efficiency and an improved signal-to-noise ratio, which subsequently results in highly accurate determination of the heart rate. This is because when the first inner surface and the second inner surface would have been made flat, a considerable portion of the light transmitted towards the light sensing element would have scattered in different directions, instead of being incident upon the light sensing element. Therefore, in order to mitigate this potential issue, the first inner surface and the second inner surface are made concave in shape. The concave curvature of the first inner surface and the second inner surface effectively captures scattered light from a wide area (i.e., from a larger angular range) and redirects the scattered light towards the light sensing element. Said concave curvature ensures that the scattered light is focused (i.e., concentrated) towards the light sensing element. Moreover, the concave geometry of the curvature of the first inner surface and the second inner surface achieves this high light transmission efficiency in a very compact manner, without requiring any additional components or a complex optical setup. The power efficiency may depend on an amount of the light transmitted towards the light sensing element (wherein the light penetrates through nose tissues to reach the light sensing element) and an amount of the (transmitted) light collected at the light sensing element. Optionally, the radius of said concave shape is iteratively determined in a manner that the transmission of the light from the light transmitting element to the light sensing element is maximized. The radius of the concave shape may also help to focus the light in a manner that increases a possibility of it being absorbed by the blood vessels inside the user's nose.

Optionally, at least one of: a first outer surface that lies opposite to the first inner surface at a first side of the first cushioning element, a second outer surface that lies opposite to the second inner surface at a second side of the second cushioning element, is coated with a light-blocking material. The technical benefit of coating the first outer surface and the second outer surface with the light-blocking material is that it prevents ambient light (such as sunlight light or artificial light) from entering the nose pad assembly, and thereby improving an accuracy of heart rate determination. This is necessary because the ambient light may adversely affect an operation of the nose pad assembly, for example, by introducing noise/interference into the light transmitted by the light transmitting element. Thus, by coating the first outer surface and the second outer surface with the light-blocking material signal-to-noise ratio could be significantly increased. The light-blocking material could be used as a light-blocking paint (such as a black-colour paint) or a light-blocking film. The light-blocking material could also be applied using thin reflective metallization.

Optionally, the light-blocking material has one of: light-absorbing properties, light-reflective properties that are similar to light-reflective properties of human skin. In this regard, the light-blocking material absorbs (namely, blocks) the ambient light incident upon the first cushioning element and the second cushioning element. This helps in improving the signal-to-noise ratio and the accuracy of heart rate determination. Alternatively, the material may have the light-reflective properties similar to those of the human skin. Notably, the human skin reflects and scatters light to some extent, and the light-blocking material having said light-reflective properties could redirect and incident the ambient light away from the first cushioning element and the second cushioning element (i.e., from entering into the nose pad assembly). This helps in improving the signal-to-noise ratio and the accuracy of heart rate determination.

It will be appreciated that an optical matching between the light and the user's skin depends on multiple factors. In an example, there could be a transparent, electrically-insulating part in between an optical path of the light (for example, due to presence of the reflective material and/or the non-reflective material that is coated with the reflective material), in addition to at least one of: air, sweat on user's skin, dirt/grease on user's skin. In such a scenario, when a non-collimated light source would be employed, a significant part of the light is lost due to a total internal reflection (TIR) at an interface between the user's skin and a given cushioning element. Therefore, in order to mitigate this potential issue, a strongly-collimated light source could be employed to yield improved power efficiency and a high signal-to-noise ratio. Even when the non-collimated light source is to be employed (which may be inexpensive and requires less power as compared to the strongly-collimated light source), it may be advantageous to employ the reflective material and/or the non-reflective material that is coated with the reflective material, as this may act as a secondary light source by reflecting the light towards the user's skin. Moreover, a concave shape of the first inner surface and the second inner surface may be optimal, but their flat shapes could also work. This is because for most part, a propagation of the light inside a nose tissue is based on light scattering phenomenon, so a direction of the light need not matter enough, as long as the light penetrates through the nose tissue. On the light sensing element, a very large skin area is relatively evenly emitting the light, and a concave shape of the second inner surface is advantageous because of similar reasons as discussed hereinabove.

Optionally, at least one of: the first inner surface, the second inner surface, a third side of the first cushioning element that touches the first side of the user's nose, a fourth side of the second cushioning element that touches the second side of the user's nose, has at least one of: a perforation, a groove, a bulge. The term "perforation" refers to small holes or openings, strategically incorporated into the cushioning elements of the nose pad assembly. The technical benefit of having the perforation (namely, a small hole or an opening) on the at least one of: the first inner surface, the second inner surface, the third side, the fourth side, is that it facilitates ventilation for the user's skin beneath the nose pad assembly, thereby mitigating potential issues associated with prolonged wear, such as excessive moisture accumulation. Additionally, having the perforation may also enable a passage for the light to be emitted by the light transmitting element or received by the light sensing element. The technical benefit of having the groove (namely, a recessed area) on the at least one of: the first inner surface, the second inner surface, the third side, the fourth side, is that it improves a flexibility of the first cushioning element and/or the second cushioning element, thereby allowing them to adapt to a shape of the user's nose more effectively. The technical benefit of having the bulge (namely, a protruding part) on the at least one of: the first inner surface, the second inner surface, the third side, the fourth side, is that it may potentially facilitate in increasing a surface area of the first cushioning element and/or the second cushioning element in contact with the user's nose. This may contribute to a more stable fit and improved contact for accurate heart rate monitoring.

In an embodiment, a light-transmitting surface of the light transmitting element faces a light-sensing surface of the light sensing element. In this regard, the light transmitting element and the light sensing element are arranged in a manner that the light emitted from the light-transmitting surface directly incident upon the light-sensing surface upon passing through the user's nose. Such an arrangement may enable in accurately measuring variations in light intensity caused by changes in the blood flow, and in determining the heart rate in a highly accurate and reliable manner. The term "light-transmitting surface" refers to a surface of the light transmitting element from where the light is emitted. The term "light-sensing surface" refers to a surface of the light sensing element at which the light is transmitted (namely, a surface of the light sensing element that is capable of sensing the light). Such an implementation has been illustrated in conjunction with FIG. 3A, for sake of better understanding and clarity.

In another embodiment, in the nose pad assembly, at least one of the following is true:

a light-transmitting surface of the light transmitting element faces the first inner surface, such that the light is redirected by the first inner surface towards the light sensing element;

a light-sensing surface of the light sensing element faces the second inner surface, such that the light is redirected by the second inner surface towards the light-sensing surface.

In some implementations, when the light-transmitting surface of the light transmitting element faces the first inner surface, and the light-sensing surface of the light sensing element faces the first inner surface, the light emitted from the light-transmitting surface incident upon the first inner surface wherefrom the light is redirected towards the light-sensing surface. In other implementations, when the light-sensing surface of the light sensing element faces the second inner surface, and the light-transmitting surface of the light transmitting element faces the second inner surface, the light emitted from the light-transmitting surface incident upon the second inner surface wherefrom the light is redirected towards the light-sensing surface. In yet other implementations, when the light-transmitting surface of the light transmitting element faces the first inner surface, as well as the light-sensing surface of the light sensing element faces the second inner surface, the light emitted from the light-transmitting surface incident upon the first inner surface wherefrom the light is redirected towards the second inner surface, wherefrom the light is again redirected towards the light-sensing surface. Such an implementation has been illustrated in conjunction with FIG. 3B, for sake of better understanding and clarity. It will be appreciated that any of the aforesaid implementations may enable in accurately measuring variations in light intensity caused by changes in the blood flow, and in determining the heart rate in a highly accurate and reliable manner.

Optionally, a directivity of the light sensing element is compatible with a directivity of the light transmitting element. In this regard, the directivity of the light-sensing element being compatible with the directivity of the light transmitting element means that a directional emission pattern of the light for the light transmitting element is complimentary to (i.e., well-synchronized with) a directional reception pattern of the light for the light sensing element. In other words, a sensitivity of the light-sensing element for the incoming light aligns with a direction in which the light transmitting element emits the light. This is because when the light travels through nose tissues (after being emitted from the light transmitting element), both a direct component and a diffuse component of the light are to be captured by the light sensing element for accurate heart rate measurement, and therefore for a maximal efficiency, the light transmitting element and the light sensing element need to be well-aligned in the aforesaid manner. Beneficially, due to this, the light emitted from the light transmitting element is effectively captured by the light sensing element upon passing through the user's nose, thereby resulting in accurate and reliable determination of the heart rate. In a scenario when the aforesaid directivities are incompatible, there would be a potential risk of suboptimal light capture by the light sensing element, leading to inaccuracies in heart rate measurements. Directivity is well-known in the art.

Optionally, at least one of: a third side of the first cushioning element that touches the first side of the user's nose and a fourth side of the second cushioning element that touches the second side of the user's nose, has a soft interface layer which is optically transparent for the light that is used for measuring the heart rate. The technical benefit of having the soft interface layer is that it facilitates in protecting optical components (such as the light transmitting element and the light sensing element) from electrical discharges and from mechanical wear/scratches, without affecting an operation of the nose pad assembly (as the soft interface layer is optically transparent). Moreover, the soft interface layer may enhance comfort of the user when the optical apparatus is to be worn by the user for extended durations. The aforesaid optical transparency of the soft interface layer may ensure that the light emitted from the light transmitting element can easily and uninterruptedly penetrate through itself, in order to incident upon the user's nose. Optionally, a finish of and/or a coating on the surface of the soft interface layer enables the first cushioning element and/or the second cushioning element to stay positioned in place with respect to the user's nose, even upon movement of the user's head. The soft interface layer may be user-replaceable, for example, like a sock that is pulled over a given cushioning element. The soft interface layer may be made up of a silicone material.

Optionally, a surface of at least one of: a third side of the first cushioning element that touches the first side of the user's nose, a fourth side of the second cushioning element that touches the second side of the user's nose, has at least one of: a rough texture, an anti-reflective coating, a refractive index that is closely-matched to a refractive index of the user's nose. It will be appreciated that having the rough texture on the surface of the at least one of: the third side, fourth side, may facilitate in improving a grip of a given cushioning element on the user's nose, which may result in a secure fit of the nose pad assembly on the user's nose. Additionally, the rough texture on the surface also minimises a risk of total internal reflection (TIR) or other reflections, thereby improving a transmission of the light from the nose pad assembly to skin of the user's nose, when the nose pad assembly is in use. The rough texture could be achieved by way of using a matte structure having a required roughness. The technical benefit of having the anti-reflective coating on the surface of the at least one of: the third side, fourth side, may facilitate in minimising glares or unwanted reflections off said surface (for example, due to ambient light). This may help in improving the signal-to-noise ratio and the accuracy of heart rate determination. Furthermore, when the refractive index of said surface is closely-matched with the refractive index of the user's nose, the light is less likely to reflect at a boundary of said surface and the user's nose and may help in achieving a same technical effect of improving the transmission of the light from the nose pad assembly to skin of the user's nose, when the nose pad assembly is in use.

Optionally, the at least one processor is further configured to:

generate a visual representation of how the heart rate of the user varies over a given time period;

provide the visual representation on a user interface of a user device associated with the user.

In this regard, once the at least one processor has determined the heart rate of the user for the given time period, the at least one processor can generate the visual representation of how the heart rate of the user i.e., how the heart rate of the user varies within the given time period. It will be appreciated that said visual representation may be a graphical representation, a pictorial representation, or other visual formats that illustrate changes in the heart rate over the given time period. It will also be appreciated that providing the visual representation on the user interface could be useful for tracking trends, identifying patterns, or continuous monitoring of the heart rate, for example, during different activities in which the user may be involved. This may facilitate a better understanding of user's cardiovascular health. The user device could, for example, be a smartphone, a tablet, a smartwatch, a laptop, and a computer. Optionally, the at least one processor is communicably coupled to the user device.

The present disclosure also relates to the optical apparatus as described above. Various embodiments and variants disclosed above, with respect to the aforementioned nose pad assembly, apply mutatis mutandis to the optical apparatus.

The present disclosure also relates to the method as described above. Various embodiments and variants disclosed above, with respect to the aforementioned nose pad assembly, apply mutatis mutandis to the method.

DETAILED DESCRIPTION OF THE DRAWINGS

Referring to FIG. 1, illustrated is a nose pad assembly 100 for measuring heart rate, in accordance with an embodiment of the present disclosure. With reference to FIG. 1, the nose pad assembly 100 is employed in the optical apparatus 102, wherein the optical apparatus is worn by a user. The nose pad assembly 100 comprises: a first cushioning element 104 and a second cushioning element 106, wherein a first inner surface 108 of the first cushioning element 104 and a second inner surface 110 of the second cushioning element 106 are capable of redirecting light; a light transmitting element 112 arranged in the first cushioning element 104; a light sensing element 114 arranged in the second cushioning element 106; and at least one processor (depicted as a processor 126) arranged in a bridge portion 118 of the optical apparatus 102, wherein when the optical apparatus 102 is worn by the user, the bridge portion 118 is in proximity of the user's nose 120 such that the first cushioning element 104 rests on a first side 122 of the user's nose 120 and the second cushioning element 106 rests on a second side 124 of the user's nose 120. Optionally, the nose pad assembly 100 further comprises an arm element 116 that physically connects the first cushioning element 104 and the second cushioning element 106 through the bridge portion 118. The processor 126 is configured to perform various operations, as described earlier with respect to the aforementioned first aspect. The processor 126 is communicably coupled to the light transmitting element 112 and the light sensing element 114.

Optionally, in the nose pad assembly 100, a first outer surface 128 lies opposite to the first inner surface 108 at a first side 130 of the first cushioning element 104, and a second outer surface 132 lies opposite to the second inner surface 110 at a second side 134 of the second cushioning element 106. The light transmitting element 112 and the light sensing element 114 are shown to be arranged in the first cushioning element 104 and the second cushioning element 106, respectively. Optionally, in the nose pad assembly 100, a third side 136 of the first cushioning element 104 touches the first side 122 of the user's nose 120, and a fourth side 138 of the second cushioning element 106 touches the second side 124 of the user's nose 120. Optionally, the light transmitting element 112 has a light transmitting surface 140, whereas the light sensing element 114 has a light-sensing surface 142.

The optical apparatus 102 comprises a frame 144 employed to hold an optical element per eye (for example, depicted an optical element 146 for a first eye, and an optical element 148 for a second eye), wherein a bridge portion 118 of the frame 144 rests on the user's nose 120 when the optical apparatus 102 is worn by the user. The nose pad assembly 100 is attached to the bridge portion 118 of the frame 144.

FIG. 1 is merely an example, which should not unduly limit the scope of the claims herein. The person skilled in the art will recognize many variations, alternatives, and modifications of embodiments of the present disclosure.

Figure 2:
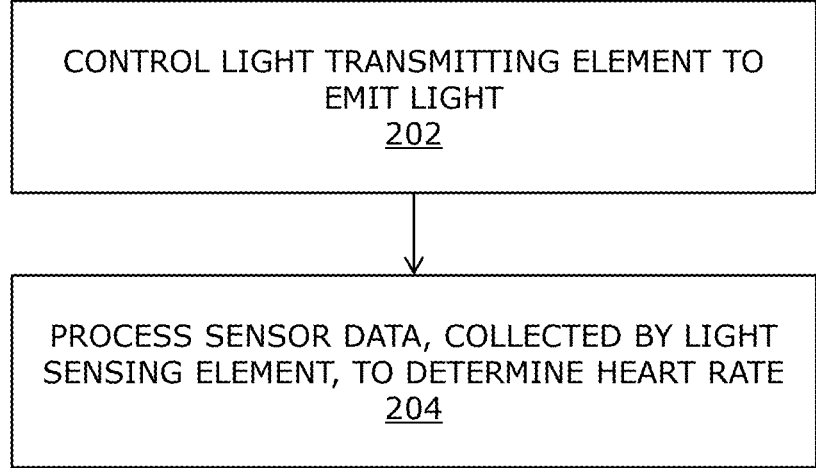
FIG. 2 illustrates steps of a method for measuring heart rate using a nose pad assembly, in accordance with an embodiment of the present disclosure.

Referring to FIG. 2, illustrated are steps of a method for measuring heart rate using a nose pad assembly, in accordance with an embodiment of the present disclosure. At step 202, a light transmitting element is controlled, wherein the light transmitting element is arranged in a first cushioning element, for emitting light, wherein the light passes through a user's nose towards a light sensing element arranged in a second cushioning element, and wherein at least a portion of the light is redirected by at least one of: a first inner surface of the first cushioning element, a second inner surface of the second cushioning element, during the said passage. At step 204, sensor data that is collected by the light sensing element, is processed by the processor for determining the heart rate of the user of an optical apparatus in which the nose pad assembly is employed.

The aforementioned steps are only illustrative and other alternatives can also be provided where one or more steps are added, one or more steps are removed, or one or more steps are provided in a different sequence without departing from the scope of the claims.

Figure 3A:
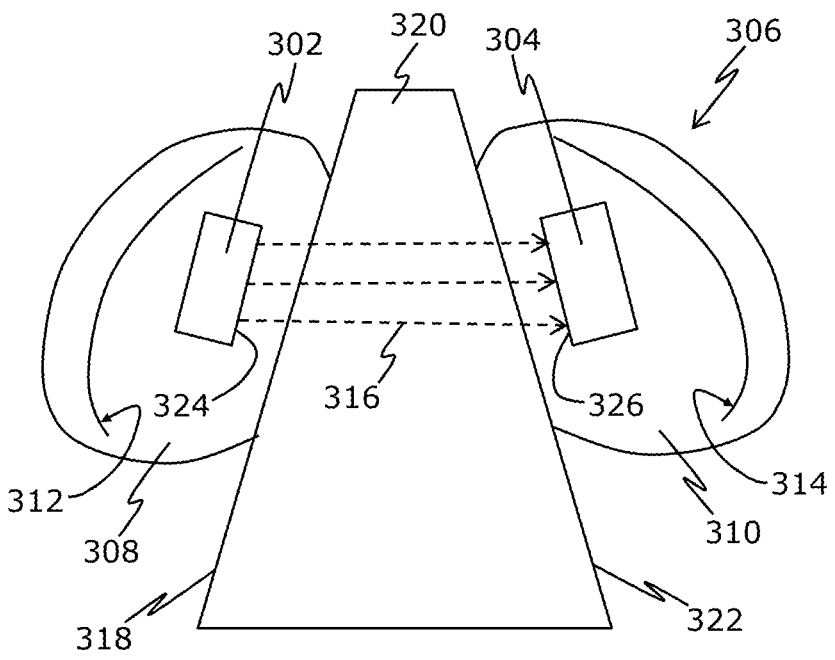
FIGS. 3A and 3B illustrate different example ways of arranging a light transmitting element and a light sensing element in a nose pad assembly, in accordance with different embodiments of the present disclosure.
Figure 3B:
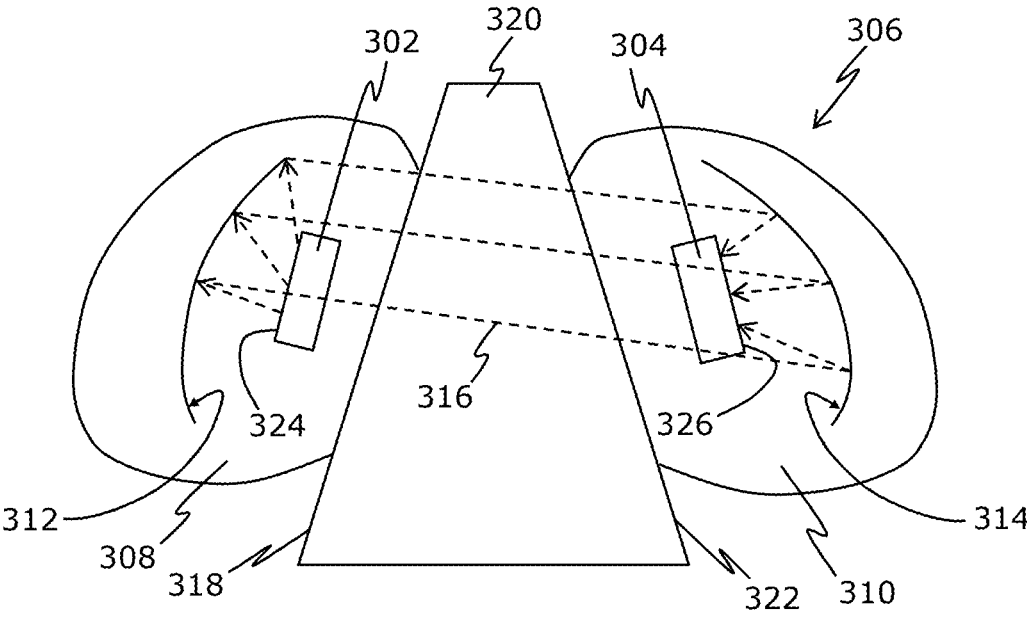

Referring to FIGS. 3A and 3B, FIGS. 3A and 3B illustrate different example ways of arranging a light transmitting element 302 and a light sensing element 304 in a nose pad assembly 306, in accordance with different embodiments of the present disclosure. With reference to FIGS. 3A and 3B, the nose pad assembly 306 is shown to comprise a first cushioning element 308, a second cushioning element 310, the light transmitting element 302, and the light sensing element 304. A first inner surface 312 of the first cushioning element 308 and a second inner surface 314 of the second cushioning element 310 are capable of redirecting light 316 (for example, such as near-infrared light, green light, red light, or white light). The first cushioning element 308 rests on a first side 318 of a user's nose 320 and the second cushioning element 310 rests on a second side 322 of the user's nose 320. The light transmitting element 302 is shown to be arranged in the first cushioning element 308. The light sensing element 304 is shown to be arranged in the second cushioning element 310. For sake of convenience and clarity, dashed lines with arrows are used for depicting an optical path of the light 316 transmitted by the light transmitting element 302 towards the light transmitting element 304.

With reference to FIG. 3A, the light transmitting element 302 and the light sensing element 304 are arranged in a manner that a light-transmitting surface 324 of the light transmitting element 302 directly faces a light-sensing surface 326 of the light sensing element 304. In this regard, the light 316 is emitted (namely, originated) from the light transmitting surface 324, and directly passes through the user's nose 320, to reach the light-sensing surface 326. With reference to FIG. 3B, the light transmitting element 302 and the light sensing element 304 are arranged in a manner that the light transmitting surface 324 faces the first inner surface 312 of the first cushioning element 308, while the light-sensing surface 326 faces the second inner surface 314 of the second cushioning element 310. In this regard, the light 316 is emitted from the light transmitting surface 324, is redirected by the first inner surface 312 towards the second inner surface 314 wherefrom the light is further redirected to incident on the light-sensing surface 326.

FIGS. 3A and 3B are merely examples, which should not unduly limit the scope of the claims herein. The person skilled in the art will recognize many variations, alternatives, and modifications of embodiments of the present disclosure. For example, only the light transmitting surface 324 of the light transmitting element 302 faces the first inner surface 312, such that the light 316 is redirected by the first inner surface 312 directly towards the light-sensing surface 326 of the light sensing element 304. Alternatively, only the light-sensing surface 326 of the light sensing element 304 faces the second inner surface 314, such that the light 316 (that is directly received from the light transmitting surface 324 of the light transmitting element 302) is redirected by the second inner surface 314 towards the light-sensing surface 326.

Figure 4:
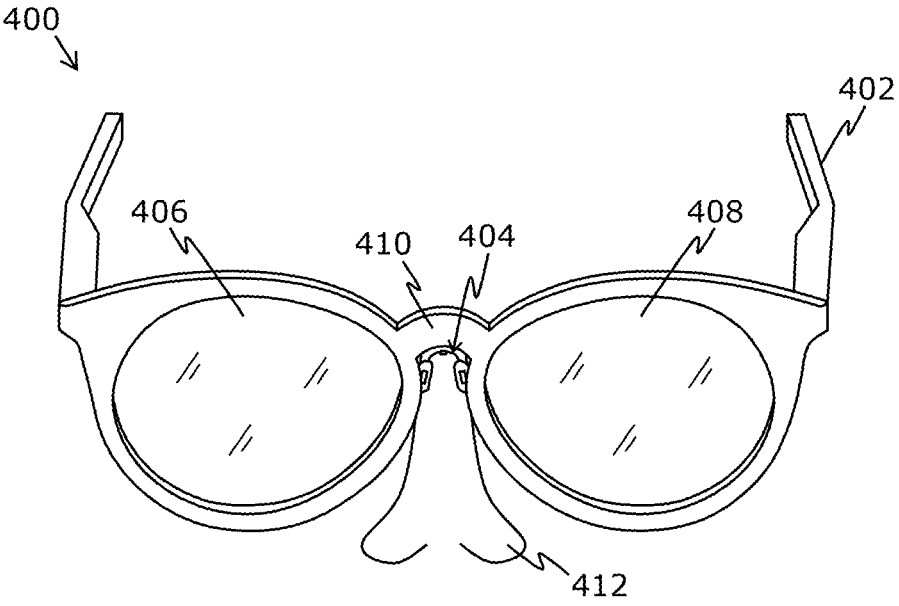
FIG. 4 illustrates a schematic illustration of an optical apparatus, in accordance with an embodiment of the present disclosure.

Referring to FIG. 4, illustrated is a schematic illustration of an optical apparatus 400, in accordance with an embodiment of the present disclosure. As shown in FIG. 4, the optical apparatus 400 comprises a frame 402, and a nose pad assembly 404. The frame 402 is employed to hold an optical element per eye (for example, depicted as optical element 406 for a first eye, and an optical element 408 for a second eye), wherein a bridge portion 410 of the frame 402 rests on a user's nose 412 when the optical apparatus 400 is worn by the user. Furthermore, the nose pad assembly 402 is shown to be attached to the bridge portion 410 of the frame 402.

FIG. 4 is merely an example, which should not unduly limit the scope of the claims herein. The person skilled in the art will recognize many variations, alternatives, and modifications of embodiments of the present disclosure.

The invention claimed is:

1. A nose pad assembly for measuring heart rate, the nose pad assembly comprising:
   a first cushioning element and a second cushioning element, wherein a first inner surface of the first cushioning element and a second inner surface of the second cushioning element are capable of redirecting light; wherein at least one of the first inner surface or the second inner surface is made of at least one of: a reflective material or a non-reflective material that is coated with a reflective material;
   a light transmitting element arranged in the first cushioning element;
   a light sensing element arranged in the second cushioning element; and
   at least one processor arranged in a bridge portion of an optical apparatus in which the nose pad assembly is employed, wherein when the optical apparatus is worn by a user, the bridge portion is in proximity of the user's nose such that the first cushioning element rests on a first side of the user's nose and the second cushioning element rests on a second side of the user's nose, wherein the at least one processor is configured to:
      control the light transmitting element to emit light, wherein the light passes through the user's nose towards the light sensing element, and wherein at least a portion of the light is redirected by at least one of: the first inner surface, the second inner surface, during said passage; and
      process sensor data, collected by the light sensing element, to determine the heart rate of the user.

2. The nose pad assembly of claim 1, wherein the first inner surface and the second inner surface are concave in shape, a radius of said concave shape being selected so as to maximize transmission of the light from the light transmitting element to the light sensing element.

3. The nose pad assembly of claim 1, wherein at least one of: the first inner surface, the second inner surface, a third side of the first cushioning element configured to touch the first side of the user's nose, a fourth side of the second cushioning element configured to touch the second side of the user's nose, has at least one of: a perforation, a groove, a bulge.

4. The nose pad assembly of claim 1, wherein a light transmitting surface of the light transmitting element faces a light-sensing surface of the light sensing element.

5. The nose pad assembly of claim 1, further comprising at least one of:
   a light transmitting surface of the light transmitting element facing the first inner surface, such that the light is redirected by the first inner surface towards the light sensing element;
   a light-sensing surface of the light sensing element facing the second inner surface, such that the light is redirected by the second inner surface towards the light-sensing surface.

6. The nose pad assembly of claim 1 wherein a directivity of the light sensing element is compatible with a directivity of the light transmitting element.

7. The nose pad assembly of claim 1, wherein the first cushioning element and the second cushioning element are removably attached to the light transmitting element and the light sensing element, respectively.

8. The nose pad assembly of claim 1, wherein a material of the first cushioning element and the second cushioning element is soft and flexible, and is only transparent for the light that is used for measuring the heart rate.

9. The nose pad assembly of claim 1, wherein the light is one of: near-infrared light, green light, red light, white light.

10. The nose pad assembly of claim 1, wherein at least one of: a third side of the first cushioning element configured to touch the first side of the user's nose and a fourth side of the second cushioning element configured to touch the second side of the user's nose, has a soft interface layer which is optically transparent for the light that is used for measuring the heart rate.

11. The nose pad assembly of claim 1, wherein a surface of at least one of: a third side of the first cushioning element configured to touch the first side of the user's nose, a fourth side of the second cushioning element configured to touch the second side of the user's nose, has at least one of: a rough texture, an anti-reflective coating, a refractive index that is closely-matched to a refractive index of the user's nose.

12. The nose pad assembly of claim 1, wherein the at least one processor is further configured to:
   generate a visual representation of how the heart rate of the user varies over a given time period;
   provide the visual representation on a user interface of a user device associated with the user.

13. The nose pad assembly of claim 1, wherein at least one of: a first outer surface that lies opposite to the first inner surface at a first side of the first cushioning element, a second outer surface that lies opposite to the second inner surface at a second side of the second cushioning element, is coated with a light-blocking material.

14. The nose pad assembly of claim 13, wherein the light-blocking material has one of: light-absorbing properties, light-reflective properties that are similar to light-reflective properties of human skin.

15. The nose pad assembly of claim 1, further comprising an arm element that is configured to physically connect the first cushioning element and the second cushioning element through the bridge portion of the optical apparatus.

16. The nose pad assembly of claim 15, wherein the arm element comprises electrical circuitry to electrically connect the light transmitting element with the at least one processor, and to electrically connect the light sensing element with the at least one processor.

17. The nose pad assembly of claim 15, wherein:

the arm element and a given cushioning element are implemented as separate individual elements, wherein the arm element is arranged on any one of: the bridge portion of the optical apparatus, a rim of a frame of the optical apparatus, or the arm element and the given cushioning element are integrated as a single element, wherein the given cushioning element is at least one of: the first cushioning element, the second cushioning element.

18. An optical apparatus comprising:

the nose pad assembly of claim 1.

19. A method for measuring heart rate using the optical apparatus of claim 18, the method comprising:

controlling the light transmitting element for emitting light, wherein the light passes through the user's nose towards the light sensing element, and wherein at least a portion of the light is redirected by at least one of: the first inner surface of the first cushioning element, the second inner surface of the second cushioning element, during said passage; and processing sensor data, collected by the light sensing element, for determining the heart rate of the user.

* * * * *